United States Patent [19]

Clayman et al.

[11] Patent Number: 4,642,116
[45] Date of Patent: Feb. 10, 1987

[54] BUOYANT POSTERIOR CHAMBER INTRAOCULAR LENS IMPLANT

[76] Inventors: Henry Clayman, Suite 709, 12555 Biscayne Blvd., Miami, Fla. 38181; James R. Longacre, 3621 Littledale Rd., Kensington, Md. 20895

[21] Appl. No.: 713,539

[22] Filed: Mar. 19, 1985

[51] Int. Cl.[4] .............................................. A61F 2/16
[52] U.S. Cl. ..................................................... 623/6
[58] Field of Search ................................ 3/13, 1; 623/6

[56] References Cited

U.S. PATENT DOCUMENTS

| | | | |
|---|---|---|---|
| Re. 31,640 | 8/1984 | Freeman | 3/13 |
| 4,010,496 | 3/1977 | Neefe | 3/13 |
| 4,074,368 | 2/1978 | Levy, Jr. et al. | 3/13 |
| 4,244,060 | 1/1981 | Hoffer | 3/13 |
| 4,285,072 | 8/1981 | Morcher et al. | 623/6 |
| 4,402,579 | 9/1983 | Poler | 3/13 X |
| 4,547,914 | 10/1985 | Castleman | 623/6 |

OTHER PUBLICATIONS

"Ovoid Optic Posterior Chamber Intraocular Lens: The First One Hundred Cases" by H. M. Clayman, Am. Intra-Ocular Implant Soc. J.-vol. 8, Fall 1982, pp. 343-345.
Laseridge-Another Innovation in IOL Design from IOLAB (advertisement), 4 pages, Oct. 1983.

Primary Examiner—Ronald L. Frinks
Attorney, Agent, or Firm—Cushman, Darby & Cushman

[57] ABSTRACT

A lens with a central optic of material denser than the aqueous humor of the eye and having a substance incorporated therein, preferably an inert gas in a bubble, of a lesser density. In one embodiment gas bubbles are incorporated in the top and bottom of an ovoid lens and in a second embodiment in an annular ridge extending outwardly from the rear surface of the lens to also space the rear surface from the posterior capsule.

12 Claims, 4 Drawing Figures

BUOYANT POSTERIOR CHAMBER INTRAOCULAR LENS IMPLANT

BACKGROUND AND SUMMARY OF THE INVENTION

The invention relates to a posterior chamber lens for implantation in the eye.

Surgical removal of opaque lenses from the eyes of cataract patients is one of the most common surgical procedures. In the past, contact lenses or spectacles were usually prescribed for the patient to provide at least limited vision following the operation. The optical and other drawbacks of contact lenses and spectacles for such purpose were numerous. Today, implantation of an artificial intraocular lens to replace the removed opaque natural lens is the preferred way to restore the patient's sight.

The natural lens in the eye serves to focus the light entering the eye through the cornea onto the retina. The lens is surrounded by a thin capsule. In cataract surgery either the entire lens, including the capsule, is removed intact in the so-called intracapsular extraction or the transparent rear wall of the capsule (so-called posterior capsule) is left in the eye in a so-called extracapsular cataract extraction. Extracapsular extraction is now the preferred technique.

The eye is divided by the iris into an anterior chamber in front of the iris and a posterior chamber behind the iris. The implant can be placed either in the anterior chamber or the posterior chamber. Placement in the posterior chamber is now preferred for a number of reasons.

One of the particular advantages of placement in the posterior chamber is that the implant need not be sutured to the eye and can be simply positioned by the use of haptic loops or the like extending from the lens body. U.S. Pat. Nos. 4,159,546 and 4,298,994 describe implants of this type described for implantation in the posterior chamber. Implants and implantation techniques are described fully in the *Surgeon's Guide to Intraocular Lens Implantation* by Henry M. Clayman, M.D. (SLACK, Inc. 1985).

The most common intraocular lens configuration utilizes polymethylmethacrylate (PMMA) with either integral haptic loops of PMMA or more commonly, haptic loops of polypropylene fixed to the central optic. One problem which has occurred with some types of intraocular lenses is downward movement of the central optic after implantation. A central optic of PMMA is denser than the aqueous humor of the eye so, if the lower haptic loop does not provide a sufficient upward force, downward movement can result in mispositioning of the central optic. The problem is even more acute with central optics of glass which for some purposes has superior optical characteristics but which is even denser than PMMA. Moreover, oscillation of the implant can occur following rapid head movements resulting in unpleasant sensations in the patient. Severe occular trauma can result in undesirable displacement of the implant. It is therefore desirable, under at least some circumstances, to improve the buoyancy of the implant and even make it float weightless in the eye.

Polypropylene has a density less than that of the aqueous humor of the eye and therefore tends to buoy the denser central optic. Polypropylene is used ubiquitously in medicine over a wide range of products without any known problems from degradation. However, its ocular use has raised special concerns because of the reported succeptibility of this material to ultra-violet (UV) degradation. Other concerns have been expressed recently concerning polypropylene in the posterior chamber where it is in apposition with uveal tissue and reports have emanated showing surface changes in the material. Polypropylene may not therefore be the ideal material for haptic loops.

Some other materials which may be more suitable for the haptic loops, however, have a density greater than the density of the aqueous humor of the eye and therefore will even further reduce the buoyancy of the implant. Some of these materials such as medical grade silicone are heat autoclavable and intraocular lenses formed entirely from medical grade silicone have been implanted in certain subjects. While the use of silicone for the central optic may be undesirable because of possible accumulation of lenticular protein deposits such material may for many lenses be preferable in the haptic loops to polypropylene.

The possible advantages of a weightless intraocular lens has been known for many years. For example, "A Weightless Iseikonic Intraocular Lens" by Richard O. Binkhorst et al, *American Journal of Ophthalmology*, Volume 58, Number 1, July 1964, pp. 73–78 describe efforts to make such a lens. The patent to Freeman, U.S. Pat. No. Re. 31,640 suggests utilizing loops or the like having a density less than the aqueous humor of the eye or attaching a hermetically sealed buoyancy chamber to the central optic to improve buoyancy. Haptic loops of reduced buoyancy are formed according to Freeman by utilizing hollow tubes or the like.

As noted above, it may be desirable under certain circumstances to utilize haptic loops having a density greater than the density of the aqueous humor. Further, it is desirable to increase the buoyancy of the central optic itself without the complexity of attaching a separate buoyant chamber.

This is achieved according to the present invention by incorporating a substance into the central optic having a density less than the density of the aqueous humor. Preferably an inert gas such as Helium or even air is incorporated in a bubble formed in the central optic.

The above-noted U.S. Pat. No. 4,295,994 to Henry M. Clayman describes an intraocular lens designed for implantation in the posterior chamber and which has a dimension in one transverse direction greater than its dimension in a perpendicular direction across the lens surface. Preferably the lens is formed as an ovoid with the long dimension extending vertically. This configuration ensures that even should the central optic sag somewhat the patient's vision will not be adversely affected. Moreover, for reasons described in the above-noted patent this configuration is under some circumstances easier to insert and has other advantages. In a lens of this type it is convenient to incorporate the gas bubbles adjacent the top and bottom of the ovoid lens where they will be clearly out of the patient's normal field of view.

Typically, the rear surface of an intraocular lens implanted in the posterior chamber contacts the posterior capsule over at least a substantial portion of its surface. This may to some extent impede the natural flow of fluids, possibly resulting in some damage to the posterior capsule. The rear surface of the lens can also to some extent abrade the posterior capsule and possibly damage that capsule.

In a small percentage of cases the naturally transparent posterior capsule becomes cloudy following implantation. In this instance the capsule must be opened so that light can be focused onto the retina. Until recently this was accomplished by inserting an instrument into the eye to cut through the posterior capsule i.e. a so-called dicission. However this operation is now very easily accomplished on an outpatient basis by the use of a Neodynium YAG laser. The coherent light from the laser is focused directly onto the posterior capsule to, in effect, form a hole in the capsule without any damage to other portions of the eye.

However, if the rear surface of an implant is in contact or closely adjacent the spot on which the laser is focused that portion of the lens will also be damaged by the laser resulting in a mark on the lens which will appear in the field of view of the patient.

The patent to Hoffer U.S. Pat. No. Re. 31,626 describes an intraocular lens designed for implantation in the posterior chamber and in which an annular lip or ridge is provided on the rear surface of the lens about the optical portion for spacing that portion from the posterior capsule. This is said to facilitate dicission by permitting an instrument to be inserted behind the lens and also to discourage or eliminate growth of lens material subsequent to extracapsular extraction.

In a lens which incorporates the portions extending outwardly from the rear surface to space the rear surface from the posterior capsule the buoyant substance, preferably an inert gas, can be incorporated into the portions for example an annular ridge. A suitable material can be chosen which focuses or directs some of the light from a YAG laser onto the posterior capsule during a dicission.

Other objects and purposes of the invention will be clear from the following detailed description of the drawings.

DETAILED DESCRIPTION OF THE DRAWINGS

Figure 1:
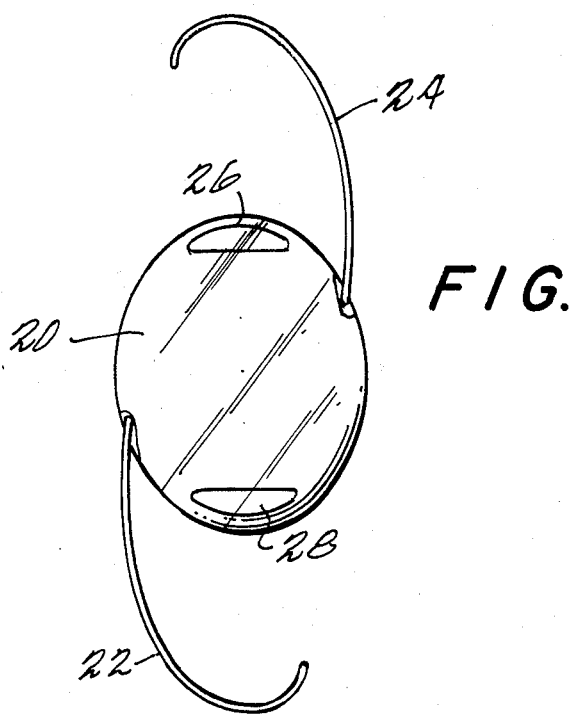
FIGS. 1 and 2 show a front and side view of a first embodiment of the present invention with inert gas bubbles incorporated in the top and bottom of an ovoid shaped lens.
Figure 2:
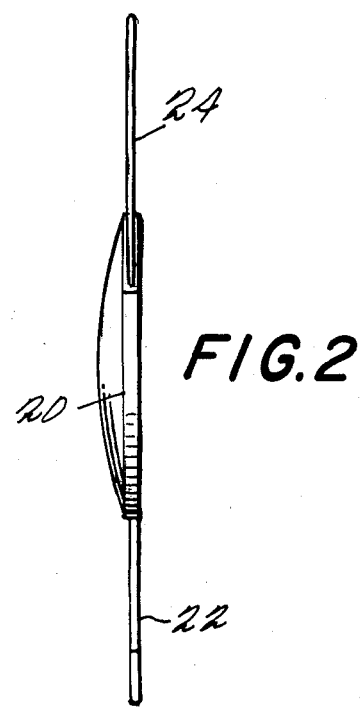

Reference is now made to FIGS. 1 and 2 which illustrate a first embodiment of the present invention. Central optic 20 is conventionally formed of PMMA, glass, a polysulfone such as polyethersulfone or some other suitable optical material having a density greater than that of the aqueous humor of the eye. A pair of J shaped haptic loops 22 and 24 are fixed to the central optic 20 and extend respectively from the bottom and top of the ovoid central optic 20. Any suitable loop shape can be employed. As indicated above, haptic loops 22 and 24 are preferably of silicone but polypropylene or other suitable material may be employed. A lens with a central optic of a polysulfone and loops of a silicone is autoclavable and advantageous for a number of reasons. The haptic loops 22 and 24 may be of a material different from central optic 20 and fixed to that optic or may be an integral extension thereof.

Bubbles 26 and 28 are formed in the central optic particularly at the top and bottom of the ovoid where they will be normally out of the field of vision of the patient. The bubbles may be of any shape and a plurality of such bubbles extending around the entire periphery of the lens may be employed. The size, number and shape of the bubbles are chosen in order to achieve any desired buoyancy. For some lenses a weightless condition may be desirable whereas for other lenses only a limited reduction in the density of the central optic 20 may be desired.

Figure 3:
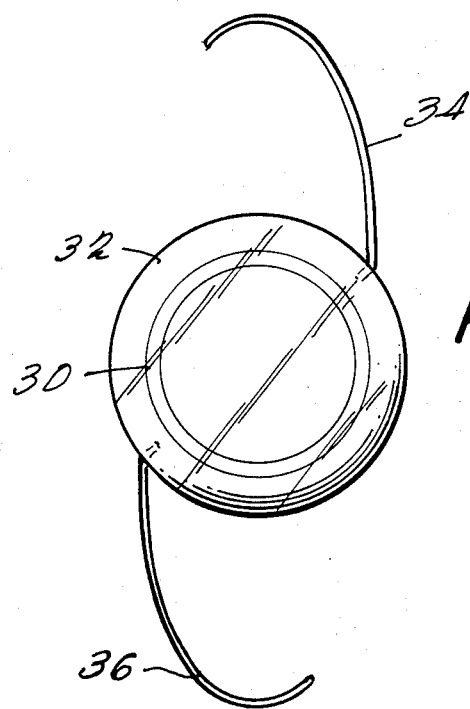
FIGS. 3 and 4 illustrate a second embodiment of the invention in which an inert gas is incorporated in an annular ridge extending outwardly from the rear surface of the central optic to space that rear surface from the posterior capsule.
Figure 4:
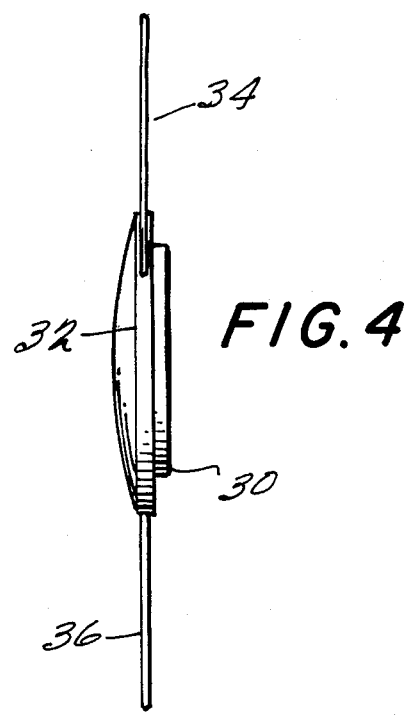

FIGS. 3 and 4 illustrate a second embodiment of the present invention in which the lesser density substance is incorporated in protrusion forming an annular ridge 30 extending outwardly posteriorly from the rear surface 32 of the central optic. This substance may also aid in directing laser radiation onto the posterior capsule during a discission. Annular ridge 30 may be broken if desired and may be either integral with the central optic 30 or attached to the same as a separate element. Ridge 30 therefore not only provides a buoyant uplift to the central optic but also serves to space the rear surface from the posterior chamber for the reasons described above. Haptic loops 34 and 36 of silicone or other suitable material are fixed to central optic 32 conventionally and as described above with regard to the embodiment of FIGS. 1 and 2.

Many changes and modifications in the above-described invention can of course be carried out without departing from the scope thereof. Accordingly, that scope is intended to be limited only by the scope of the appended claims.

What is claimed is:

1. A posterior chamber intraocular lens implant comprising:

a central optic of material denser than aqueous humor of the eye and having an annular ridge extending posteriorly from the rear surface of said central optic for spacing said central optic from the posterior capsule with a gas contained within said annular ridge of density less than the aqueous humor; and means extending outwardly from said central optic for positioning the central optic in the posterior chamber.

2. An implant as in claim 1 wherein said gas is Helium.

3. An implant as in claim 1 wherein said gas is air.

4. An implant as in claim 1 wherein said means include haptic loops of said central optic.

5. An implant as in claim 4 wherein said haptic loops are fixed to said central optic.

6. An implant as in claim 4 wherein said haptic loops are formed from a medical grade silicone.

7. An implant as in claim 1 wherein said central optic is formed of polymethymethacrylate.

8. An implant as in claim 1 wherein said central optic is formed of a polysulfone.

9. An implant as in claim 8 wherein said polysulfone is polyethersulfone.

10. An implant as in claim 1 wherein said optic is formed of glass.

11. A posterior chamber intraocular lens implant comprising:

a central optic of material denser than the aqueous humor of the eye and having a gas bubble incorporated therein in an annular ridge extending posteriorly from the rear surface of said central optic to space the rear surface from the posterior capsule and at least first and second haptic loops extending outwardly from said central optic for positioning said optic in the posterior chamber.

12. An implant as in claim 11 wherein said loops are of silicone.

* * * * *